United States Patent [19]

Collington et al.

[11] Patent Number: 5,229,418

[45] Date of Patent: Jul. 20, 1993

[54] CARBOXYLIC ACID DERIVATIVES

[75] Inventors: Eric W. Collington, Knebworth; John W. Clitherow, Sawbridgeworth; David E. Bays, Ware, all of England

[73] Assignee: Glaxo Group Limited, London, England

[21] Appl. No.: 691,399

[22] Filed: Apr. 25, 1991

[30] Foreign Application Priority Data

Apr. 26, 1990 [GB] United Kingdom ............. 9009437

[51] Int. Cl.[5] ............ A61K 31/615; A61K 31/41; C07D 307/02; C07D 249/00
[52] U.S. Cl. ............................ 514/471; 514/383; 548/262.2; 548/266.6; 549/491; 549/492
[58] Field of Search ............. 549/495; 514/471

[56] References Cited

U.S. PATENT DOCUMENTS

| | | | |
|---|---|---|---|
| 4,233,302 | 11/1980 | Martin-Smith et al. | 549/492 |
| 4,255,440 | 3/1981 | Price et al. | 549/492 |
| 4,460,506 | 7/1984 | Bradshaw | 549/492 |
| 4,613,596 | 9/1986 | Moroni | 549/492 |
| 5,075,301 | 12/1991 | Sasho et al. | 549/492 |

FOREIGN PATENT DOCUMENTS

| | | | |
|---|---|---|---|
| 269315 | 6/1988 | European Pat. Off. | 549/492 |
| 282132 | 9/1988 | European Pat. Off. | |
| 1375133 | 2/1988 | U.S.S.R. | 549/492 |
| 2006771A | 5/1979 | United Kingdom . | |
| 1565966 | 4/1980 | United Kingdom . | |
| 2220937A | 1/1990 | United Kingdom . | |

*Primary Examiner*—Cecilia Tsang
*Attorney, Agent, or Firm*—Bacon & Thomas

[57] ABSTRACT

The invention relates to a salt of a basic histamine $H_2$-receptor antagonist of formula (I)

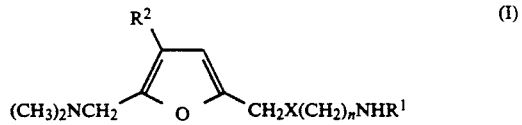

and a complex of bismuth with a carboxylic acid selected from tartaric acid, citric acid and alkyl citric acids, or a solvate of such a salt, wherein
$R^1$ represents a group of formula

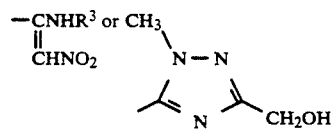

where $R^3$ represents methyl or the group $(CH_2)_2CONR^4R^5$ in which $R^4$ and $R^5$ both represent ethyl groups;
$R^2$ represents a hydrogen atom or, when $R^1$ is the group $-C(=CHNO_2)NHCH_3$, $R^2$ may also represent a methyl group; and
n is 3 and X is oxygen, or n is 2 and X is $CH_2$ or sulphur;
with the provisos that
(i) when $R^1$ represents

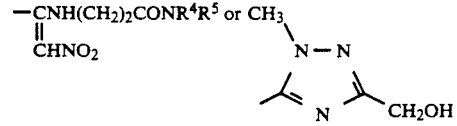

then X is sulphur and n is 2:
(ii) when $R^1$ represents $-C(=CHNO_2)NHCH_3$ and $R^2$ is hydrogen, then X is oxygen and n is 3 or X is $CH_2$ and n is 2; and
(iii) when $R^1$ represents $-C(=CHNO_2)NHCH_3$ and $R^2$ is methyl, then X is oxygen and n is 3 or X is sulphur and n is 2.

The salts and solvates thereof are useful in the treatment of gastro-intestinal disorders, such as peptic ulcer disease, gastritis and non-ulcer dyspepsia.

6 Claims, No Drawings

CARBOXYLIC ACID DERIVATIVES

This invention relates to salts of furan derivatives having antagonist activity at histamine H$_2$-receptors, to a process for the preparation thereof, to pharmaceutical compositions containing them and to their use in therapeutics. More particularly the invention is concerned with salts of certain furan derivatives formed with bismuth complexes of carboxylic acids.

Compounds which have antagonist activity at histamine H$_2$-receptors are used in the treatment of conditions where there is an advantage in lowering gastric acidity. Such conditions include duodenal and gastric ulceration, reflux oesophagitis and Zollinger-Ellison syndrome. H$_2$-receptor antagonists may also be used prophylactically in surgical procedures, and in the treatment of allergic and inflammatory conditions where histamine is a known mediator.

Bismuth salts and preparations, such as bismuth citrate, bismuth and ammonium citrate, sodium bismuthyl tartrate, acid bismuth sodium tartrate, acid solution of bismuth, concentrated solution of bismuth, and solution of bismuth and ammonium citrate, which are described in for example the British Pharmaceutical Codex (1949), have long been used as antacids in the treatment of hyperacidity and dyspepsia. In addition, before the advent of histamine H$_2$-antagonists, by which they have now essentially been superceded, such bismuth preparations were also used in the treatment of gastrointestinal ulcers.

In recent years evidence has emerged that *Campylobacter pylori* (now known as *Helicobacter pylori*) is associated with histological gastritis, non-ulcer dyspepsia and hypochlorhydria, and may be involved in the pathogenesis of gastric and duodenal ulcer disease.

*Campylobacter pylori* is susceptible to bismuth compounds such as bismuth subcitrate (in the form of, for example, tripotassium dicitrato bismuthate) and bismuth subsalicylate.

According to published European Patent Specification No. 282132, a bismuth-containing agent, preferably a Campylobacter—inhibiting bismuth-containing agent such as bismuth subsalicylate or bismuth subcitrate, may be co-administered with a H$_2$-receptor antagonist, preferably cimetidine or ranitidine, for the treatment of gastrointestinal disorders. The two active ingredients may be given as separate preparations which may be administered concurrently or non-concurrently, or may be contained in a single composition.

A number of the bismuth compounds described previously as antacids and/or agents for the inhibition of *Campylobacter pylori* are acidic complexes formed between bismuth and a carboxylic acid such as citric or tartaric acid or salts thereof with ammonia or an alkali metal.

Published UK Patent Specification No. 2220937A discloses salts of the H$_2$-receptor antagonist ranitidine and a complex of bismuth with a carboxylic acid such as citric or tartaric acid.

It has now been found that other basic H$_2$-receptor antagonists will form salts with such complexes, and the resulting products possess a useful and advantageous profile of activity.

The present invention thus provides novel salts of a basic H$_2$-receptor antagonist furan derivative of formula (I)

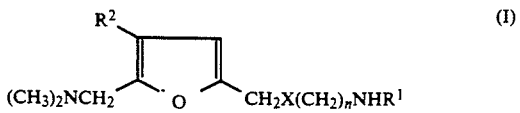

and a complex of bismuth with a carboxylic acid selected from tartaric acid, citric acid or an alkyl citric acid, and solvates of such salts.

In formula (I) R$^1$ represents the group

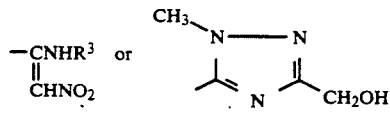

[where R$^3$ represents methyl or the group (CH$_2$)$_2$CONR$^4$R$^5$ (in which R$^4$ and R$^5$ both represent ethyl groups)]; R$^2$ represents a hydrogen atom or, when R$^1$ is the group —C(=CHNO$_2$)NHCH$_3$, R$^2$ may also represent a methyl group; and n is 3 and X is oxygen, or n is 2 and X is CH$_2$ or sulphur; with the provisos that
(i) when R$^1$ represents

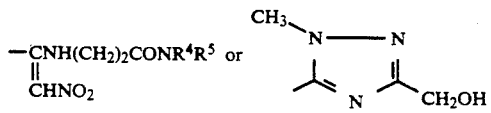

then X is sulphur and n is 2;
(ii) when R$^1$ represents —C(=CHNO$_2$)NHCH$_3$ and R$^2$ is hydrogen, then X is oxygen and n is 3 or X is CH$_2$ and n is 2; and
(iii) when R$^1$ represents —C(=CHNO$_2$)NHCH$_3$ and R$^2$ is methyl, then X is oxygen and n is 3 or X is sulphur and n is 2.

The alkyl citric acid may be for example a C$_{1-6}$alkyl citric acid, more particularly a C$_{1-3}$alkyl citric acid (e.g. propylcitric acid).

In instances where the carboxylic acid can exhibit optical and/or geometric isomerism, the invention is intended to include all optical isomers including racemates, and/or geometric isomers. Solvates, including hydrates, are also included within the scope of the invention.

The preferred carboxylic acid for use in the invention is citric acid.

A preferred group of compounds of formula (I) for use according to the invention are those in which R$^1$ represents —C(=CHNO$_2$)NHCH$_3$, n is 3 and X is oxygen, particularly the compound in which R$^2$ is hydrogen.

A further preferred group of compounds of formula (I) for use according to the invention are those in which R$^2$ represents a hydrogen atom, X is sulphur, n is 2, and R$^1$ represents the group

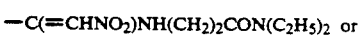

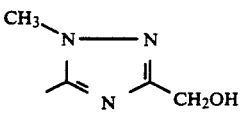

more particularly the compound in which R$^1$ represents the group

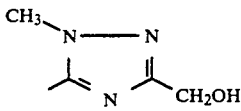

Yet another preferred group of compounds of formula (I) for use according to the invention are those in which $R_1$ represents $-C(=CHNO_2)NHCH_3$ and $R^2$ is methyl, and either X is oxygen and n is 3, or X is sulphur and n is 2, more particularly the compound in which X is sulphur and n is 2.

A preferred salt according to the invention is N-[3-[[5-[(dimethylamino)methyl]-2-furanyl]methoxy]-propyl]-N'-methyl-2-nitro-1,1-ethenediamine 2-hydroxy-1,2,3-propanetricarboxylate bismuth (3+) complex.

Further preferred salts according to the invention are N-[2-[[[5-[(dimethylamino)methyl]-4-methyl-2-furanyl]-methyl]thio]ethyl]-N'-methyl-2-nitro-1,1-ethenediamine 2-hydroxy-1,2,3-propanetricarboxylate bismuth (3+)complex, and 5-[[2-[[[5-[(dimethylamino)methyl]-2-furanyl]methyl]thio]ethyl]amino]-1-methyl-1H-1,2,4-triazole-3-methanol 2-hydroxy-1,2,3-propanetricarboxylate bismuth (3+)complex.

Salts according to the invention possess a particularly advantageous combination of properties for the treatment of gastrointestinal disorders, especially peptic ulcer disease and other gastroduodenal conditions, for example gastritis and non-ulcer dyspepsia.

Salts according to the invention thus possess the $H_2$-antagonist antisecretory properties associated with the $H_2$-receptor antagonist, together with antibacterial activity against *Helicobacter pylori*. In addition, salts of the invention possess cytoprotective properties. They also display activity against the human gastric pepsins, with preferential inhibition of pepsin 1, a pepsin isozyme associated with peptic ulcer.

The antisecretory activity of compounds according to the invention may be demonstrated in vivo against histamine-induced gastric acid secretion in the Heidenhain pouch dog. The antibacterial activity of the salts against *Helicobacter pylori* has been demonstrated in vitro. Their ability to inhibit human pepsins may be demonstrated in vitro, and cytoprotective activity may be demonstrated in vivo by the ability of the salts to inhibit ethanol-induced gastric lesions in rats.

A further feature of the salts according to the invention is that they provide a means of increasing the solubility of bismuth under aqueous conditions. Under normal circumstances many bismuth salts and complexes, including those formed with carboxylic acids of the type used in forming salts of the invention, are insoluble. Bismuth citrate, for example, has a solubility (under neutral aqueous conditions) of only 0.2% on a weight to volume (w/v) basis, whereas the salts of the invention are significantly more soluble.

Salts according to the invention are distinct chemical entities which can be distinguished from simple mixtures of the basic $H_2$-receptor antagonist and a complex of bismuth and a carboxylic acid. This distinction may be demonstrated on the basis of, for example, infra-red spectroscopy.

Salts according to the invention may be prepared by reacting the $H_2$-receptor antagonist of formula (I) with an appropriate bismuth-carboxylic acid complex (e.g. bismuth citrate or bismuth ammonium citrate), in a suitable solvent such as water, and separating the salt thus formed from the mixture. In general the resulting products are free flowing solids which are stable under normal conditions.

According to a further aspect the invention provides a salt of a basic $H_2$-receptor antagonist of formula (I) and a complex of bismuth with tartaric acid, citric acid or an alkyl citric acid, including solvates of such salts, said salt being prepared by reacting the $H_2$-antagonist of formula (I) with an appropriate bismuth-carboxylic acid complex.

The reaction between the $H_2$-receptor antagonist and an appropriate bismuth-carboxylic acid complex to give a salt according to the invention is preferably carried out at elevated temperature for example at a temperature within the range of 40° to 100° C. Once the reaction is complete (when, for example, the mixture has reached neutrality as judged by pH and/or dissolution is complete), the suspension or solution is cooled and filtered, and the required salt may be obtained from the filtrate, by evaporation followed by extraction and trituration of the resulting residue using for example an alcohol e.g. methanol or ethanol, a ketone e.g. acetone or an ether e.g. diethyl ether. Alternatively, the reaction mixture may be evaporated directly, followed by extraction and trituration of the resulting residue.

The intermediate bismuth-carboxylic acid complexes may in general be prepared by the procedures described in the British Pharmaceutical Codex (1949) and in published UK Patent Specification No. 2220937A.

The salts according to the invention may be formulated for administration in any convenient way and the invention includes within its scope pharmaceutical compositions containing a salt according to the invention adapted for use in human or veterinary medicine. Such compositions, which are primarily intended for oral administration, may be formulated in a conventional manner using one or more pharmaceutically acceptable carriers or excipients.

For oral administration, the pharmaceutical compositions may take the form of, for example, tablets (including chewable or suckable tablets) or capsules (of either the hard or soft type). Such compositions may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Tablets represent a preferred type of composition for oral use.

A proposed dose of the salts of the invention for internal administration to man is 100 mg to 1 g, preferably 100 mg to 800 mg. The unit dose may be administered, for example, one to four times daily, preferably once or twice. The exact dose will depend on the nature and severity of the condition being treated, and it will also be appreciated that it may be necessary to make routine variations to the dosage depending on the age and weight of the patient.

Certain of the basic $H_2$-receptor antagonists of formula (I) are novel, more particularly compounds covered by the formula (II)

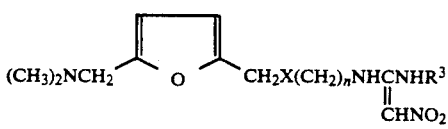 (II)

in which
X is oxygen, n is 3 and $R^3$ represents a methyl group; or
X is sulphur, n is 2 and $R^3$ represents the group $-(CH_2)_2CON(C_2H_5)_2$.

Compounds of formula (II) and physiologically acceptable salts and solvates thereof constitute a further aspect of the invention.

Suitable physiologically acceptable salts include acid addition salts formed with inorganic or organic acids such as hydrochloride, hydrobromide, sulphate, alkyl- or arylsulphonate (e.g. methanesulphonate or p-toluenesulphonate), phosphate, acetate, maleaste, succinate, citrate, tartrate, fumarate, benzoate and ascorbate salts. Solvates include hydrates.

Compounds of formula (II) may be prepared by displacement of a leaving group in a reaction involving an appropriate amine.

Thus, for example, the compound of formula (II) in which X is oxygen, n is 3 and $R^3$ represents a methyl group may be prepared by reacting the amine of formula (III)

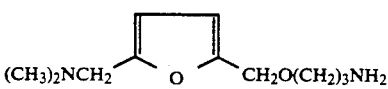 (III)

with a compound of formula (IV)

 (IV)

in which L represents a leaving group.

The reaction may be carried out in a solvent such as water or an alcohol (e.g. ethanol) or mixtures thereof, conveniently at room temperature. Alternatively the amine (III) and the compound of formula (IV) may be heated together in the absence of a solvent at a temperature of for example 80° to 100° C.

The amine of formula (III) may be used as the free base, or in the form of a salt with an organic or inorganic acid e.g. as an acetate or hydrochloride salt.

The compound of formula (II) in which X is sulphur, n is 2 and $R^3$ represents the group $-(CH_2)_2CON(C_2H_5)_2$ may be prepared by reacting a compound of formula (V)

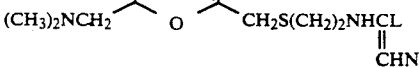 (V)

(in which L represents a leaving group) with the amine of formula (VI)

$$H_2N(CH_2)_2CON(C_2H_5)_2 \quad (VI)$$

The reaction may be carried out in a suitable solvent such as dimethylformamide or water, conveniently at room temperature.

In the above compounds (IV) and (V), the leaving group L may be, for example, a halogen atom or a $C_{1-4}$ alkoxy (e.g. ethoxy) or 3,5-dimethylpyrazolyl group or, more preferably, a $C_{1-4}$alkylthio (e.g. methylthio) group.

If a salt of the $H_2$-antagonist of formula (II) is required, this may be obtained from the free base using conventional methods. Thus for example, appropriate quantities of the free base of formula (II) and an appropriate acid, e.g. hydrochloric acid, may be mixed in a suitable solvent(s), e.g. an alcohol such as ethanol or isopropanol, or an ester such as ethyl acetate.

The invention is illustrated by the following examples, in which temperatures are in ° C. Thin layer chromatography (t.l.c.) was carried out on silica, eluting with the solvent system indicated; u.v., iodoplatinate and potassium permanganate were used for detection of the products unless otherwise indicated.

PREPARATION 1

N-[3-[[5-[(Dimethylamino)methyl]-2-furanyl]methoxy]-propyl]-N'-methyl-2-nitro-1,1-ethenediamine A suspension of N-methyl-1-(methylthio)-2-nitroethene (0.81 g) in a solution of 5-[(3-aminopropoxy)methyl]-N,N-dimethyl-2-furanmethanamine (1.06 g) in water (8 ml) was stirred at room temperature for 3 days. The solution was evaporated to dryness under reduced pressure and the oily residue re-evaporated with ethanol (3×10 ml) to give an oil. This was dissolved in methanol: 0.88 ammonia (79:1) and the solution eluted through a silica/methanol:0.88 ammonia (79:1) column. Evaporation of the appropriate eluate gave the title compound (1.02 g) as a yellow oil. T.l.c. (Methanol:0.88 ammonia; 79:1) Rf 0.55.

Analysis Found: C,52.85; H,7.64; H,17.68. $C_{14}H_{24}N_4O_4.0.25$ $H_2O$ requires C,53.07; H,7.79; N,17.68%

PREPARATION 2

3-[[1-[[2-[[[5-[(Dimethylamino)methyl]-2-furanyl]methyl]-thio]ethyl]amino]-2-nitroethenyl]amino]-N,N-diethylpropanamide dihydrochloride A solution of N-[2-[[5-[(dimethylamino)methyl]-2-furanyl]methyl]thio]ethyl]-1-methylthio-2-nitroetheneamine (2.0 g) and 3-amino-N,N-diethylpropanamide (0.72 g) in dry dimethylformamide (10 ml) was stirred at room temperature for 3 days with nitrogen bubbling through the solution. The residue was adsorbed on silica and purified by flash column chromatography on silica gel eluting with dichloromethane/methanol 9:1 to give a yellow gum (1.4 g). A solution of the gum in ethyl acetate (75 ml) was treated with excess ethereal hydrogen chloride. The solvent was decanted and the residue was triturated in dry ether (150 ml). The resulting solid was filtered-off, under nitrogen, washed with dry ether, and dried under vacuum to give the title compound (1.13 g) as a beige solid m.p. 74°–78° C. T.l.c. (Dichloromethane:ethanol:ammonia, 50:8:1) Rf 0.40;

Analysis Found C,44.7; H,7.6; N,12.9; Cl,12.9; S, 6.0. $C_{19}H_{33}N_5O_4S.2HCl.0.2C_4H_8O_2.0.7H_2O$ requires C,44.8; H,7.2; N,13.2; Cl,13.4; S,6.0%

Water assay indicated 0.7 mole $H_2O$. N.m.r. indicated 0.2 mole ethyl acetate.

EXAMPLE 1

N-[3-[[5-[(Dimethylamino)methyl]-2-furanyl]methoxy]-propyl]-N'-methyl-2-nitro1,1-ethenediamine [2-hydroxy-1,2,3-propanetricarboxylate bismuth (3+) complex (1:1)] (1:2)

A mixture of N-[3-[[5-[(dimethylamino)methyl]-2-furanyl]methoxy]propyl]-N'methyl-2-nitro-1,1-ethenediamine (2.79 g) and 2-hydroxy-1,2,3-propanetricarboxylate bismuth (3+) complex (1:1) (bismuth citrate; 2.37 g) in water (5 ml) and ethanol (2 ml) was heated at 95°–98° with stirring. After 1 h, further bismuth citrate (1.2 g) was added to the clear viscous solution and the heating continued for a further two hours with the occasional addition of small volumes (0.5 ml) of water. The mixture was diluted with water (50 ml) and the suspension filtered. The residue was washed with water to give a solid (0.923 g) consisting of bismuth citrate.

The aqueous filtrate was evaporated to dryness to give a gummy residue. The was re-evaporated with methanol (40 ml) and the residue mixed with methanol (70 ml). The suspension was heated to boiling and the solid residue triturated. The mixture was filtered and the solid residue triturated with methanol and dried at 70° C. to give the title compound (2.902 g) as a solid.

Analysis Found: C,29.07; H,3.48; N,5.46; O,26.53. $C_{14}H_{24}N_4O_4: C_6H_5O_7Bi:H_2O$. 1:1.8:0.43 requires: C,28.73; H,3.29; N,5.40; O,26.28%.

N.m.r. indicated base component:bismuth citrate, 1:1.8.

Water assay indicated 0.76% $H_2O \equiv 0.43$ mole $H_2O$.

T.l.c. (Dicholoromethane:ethanol:0.88 ammonia; 50:8:1) Rf 0.6 (base component) and Rf zero (bismuth citrate).

T.l.c. (Chloroform:methanol:acetic acid:water, 15:5:1:1) Rf 0.3 (base component) and Rf zero (bismuth citrate), detection: u.v., iodoplatinate and bromocresol green stain.

EXAMPLE 2

3-[[1-[[2-[[[5-[(Dimethylamino)methyl]-2-furanyl]methyl]-thio]ethyl]amino]2-nitroethenyl]amino]-N,N-diethylpropanamide [2-hydroxy-1,2,3-propanetricarboxylate bismuth (3+)complex (1:1)] (1:2:3)

3-[[1-[[2-[[[5-[(Dimethylamino)methyl]-2-furanyl]methyl]thio]ethyl]amino]-2-nitroethenyl]amino]-N,N-diethylpropanamide (2.0 g) and bismuth citrate (1.24 g) were mixed in water (ca. 50 ml) and heated to 100° for 1 h. After slight cooling and dilution with water (ca. 30 ml), the mixture was filtered. The small amount of residue was discarded, the filtrate evaporated to give an orange oil and then co-evaporated with methanol (2×50 ml). Further methanol (ca. 200 ml) was added to the sticky foam and the mixture heated to boiling on a steam bath for approximately 10 min when precipitation occurred. After leaving to stand for 30 min, the solid was filtered off and dried to give the title compound (899 mg) as a beige powder. $^1$H-N.m.r.δ ($D_2O$/DCl) 6.7(1H,m), 6.42(1H,m), 4.38(2H,s), 3.9-3.6(6H,s+3×m), 3.38(4H,br), 3.05(2H,½AB), 3.0-2.8(1OH, s+m+½AB) and 1.2-1.0(6H, 2×brt).

Analysis Found: C,29.O; H,3.6; N,5.11; S,2.4; Bi,35.2. $C_{19}H_{33}N_5O_4S:C_6H_5BiO_7:H_2O$(1:2.3:2) requires C,28.56;N,3.54;N,5.08; S,2.32; Bi,34.85%.

Water assay indicated 2.74% w/w $H_2O \equiv 2.0$ mol $H_2O$.

EXAMPLE 3

N-[2-[[[5-[(Dimethylamino)methyl]-4-methyl-2-furanyl]methyl]-thio]ethyl]-N'-methyl-2-nitro-1,1-ethenediamine 2-hydroxy-1,2,3-propanetricarboxylate bismuth (3+)complex (1:1)] (1:1)

To a solution of N-[2-[[[5-[(dimethylamino)methyl]-4-methyl-2-furanyl]methyl]thio]ethyl]-N'-methyl-2-nitro-1,1-ethenediamine (6.465 g) in water (25 ml) was added bismuth citrate (7.84 g) and the mixture heated at 100° for 4 hours. The suspension was filtered and the residue washed well with water then ethanol and dried to give a solid consisting of unchanged bismuth citrate (2.448 g) which was discarded. The combined filtrate and washings were evaporated to dryness with the aid of methanol (3×50 ml) then ethanol (2×50 ml). The residue was mixed with cold ethanol (70 ml) and triturated to a fine cream which was filtered off, washed with ethanol (4×5 ml) and then ether and dried to give the title compound (9.187 g).

Analysis Found: C,32.27; H, 4.19; N,7.08; O,24.13; S,4.19; Bi,27.30. $C_{14}H_{24}N_4O_3S:C_2H_5OH:C_6H_5BiO_7:H_2O$ (1:0.33:1:1.1) requires C,32.58; H,4.39; N,7.36; O,24.01; S,4.21; Bi 27.44%.

Water assay indicated 2.71% w/w $H_2O \equiv 1.09$ mole $H_2O$.

T.l.c. (Dichloromethane:ethanol:0.88 ammonia; 70:8:1)Rf 0.4 (base component) and Rf zero (bismuth citrate), detection u.v., iodoplatinate, potassium permangante and bromocresol green stain.

EXAMPLE 4

N-[4-[5-[(Dimethylamino)methyl]-2-furanyl]-butyl]-N'-methyl-2-nitro-1,1-ethenediamine [2-hydroxy-1,2,3-propanetricarboxylate bismuth (3+)complex (1:1)] (1:2)

N-[4-[5-[(Dimethylamino)methyl]-2-furanyl]butyl]-N'-methyl-2-nitro-1,1-ethenediamine (1.0 g) and bismuth citrate (0.94 g) were mixed in water and heated at 100° for 1 h. The mixture was cooled, diluted with water and the small amount of solid filtered off and discarded. The filtrate was evaporated to dryness to give an orange/yellow oil which was co-evaporated with methanol (3×40 ml). Further methanol (ca. 60 ml) was added and the mixture heated repeatedly to boiling until solidification occurred. The resulting solid was filtered off, washed well with methanol and dried to give the title compound as a buff powder (596 mg). $^1$H-N.m.r. δ ($D_2O$) 6.5(1H,d), 6.06(1H,d), 4.19(2H, s), 3.39 and 3.24 (2H, 2×tr), 2.99 and 2.89 (3H, 2×s, 2.9 (2H, ½AB), 2.71(6H, s), 2.58(2H, m) and 1.59(4H,m).

Analysis Found: C,28.1; H,3.4; N,5.15; O,26.0: Bi, 37,55. $C_{14}H_{24}N_4O_3:C_6H_5BiO_7:H_2O$(1:2:1.3) requires: C,28.0; H,3.3; N,5.0; O.26.2; Bi,37.45%.

Water assay indicated 2.17% w/w $H_2O \equiv 1.3$ mol $H_2O$.

EXAMPLE 5

5-[[2-[[[5-[(Dimethylamino)methyl]-2-furanyl]methyl]thio]ethyl]amino]-1-methyl-1H-1,2,4-triazole-3-methanol [2-hydroxy-1,2,3-propanetricarboxylate bismuth (3+) complex (1:1)](1:1)

5-[[2-[[[5-[(Dimethylamino)methyl]-2-furanyl]methyl]thio]ethyl]amino]-1-methyl-1H-1,2,4-triazole-3-methanol (2.94 g) was dissolved in water (5 ml) and bismuth citrate (3.60 g) added. The mixture was heated at 95°–98° for 3 hours and further 5-[[2-[[[5-[(dimethylamino)methyl]-2-furanyl]methyl]thio]ethyl]amino]-1-methyl-1H-1,2,4-triazole-3-methanol (0.74 g) added. The mixture was heated at 95°–98° for a further 3 hours then filtered and the residue washed free of soluble material. The combined filtrate and washings were evaporated in vacuo with the aid of methanol to give a gummy residue. This was heated with ethanol (30 ml) and the mixture evaporated to dryness. The residue was resuspended in ethanol (30 ml) and evaporated twice more and then mixed with ethanol (30 ml) and the solid triturated to a cream. The fine suspension was filtered and the residue washed with ethanol (total volume used, 60 ml), then ether and dried at 60° in vacuo to give the title compound (4.25 g).

Analysis Found: C,30.95; H,3.82; N,8.46; S,3.91; Bi, 28.7. $C_{14}H_{23}N_5O_2S:C_2H_5OH:(C_2H_5)_2O:H_2O:C_6H_5Bi-O_7(1:0.07:0.07:1.43: 1.14)$ requires C,31.39; H,4.05; N,8.61; S,3.94; Bi,29.29%.

Water assay indicated 3.56% w/w $H_2O \equiv 1.43$ mole $H_2O$

T.l.c. (Dichloromethane:ethanol: 0.88 ammonia, 50:8:1) Rf 0.4 (base component) and Rf zero (bismuth citrate), detection u.v., iodoplatinate, potassium permanganate and bromocresol green.

The following Examples A to D illustrate pharmaceutical compositions according to the invention in which the active ingredient is in particular an $H_2$-antagonist bismuth citrate as defined by formula (I). Other bismuth carboxylates according to the invention may be formulated in a similar manner.

EXAMPLE A

Tablets

Tablets may be prepared by the normal methods such as direct compression or wet granulation.

The tablets may be film coated with suitable film forming materials, such as hydroxypropyl methylcellulose, using standard techniques.

| (i) Direct Compression | mg/tablet |
| --- | --- |
| Active ingredient | 450 |
| Lactose | 133 |
| Microcrystalline Cellulose | 130 |
| Cross-linked Polyvinylpyrrolidone | 30 |
| Magnesium Stearate | 7 |
| Compression weight | 750 mg |

The active ingredient, microcrystalline cellulose, lactose and cross-linked polyvinylpyrrolidone are sieved through a 500 μm sieve and blended in a suitable mixer. The magnesium stearate is sieved through a 250 μm sieve and blended with the active blend. The blend is compressed into tablets using suitable punches.

| (ii) Wet Granulation | mg/tablet |
| --- | --- |
| Active ingredient | 450 |
| Lactose | 138 |
| Pregelatinised Starch | 75 |
| Cross-linked Polyvinylpyrrolidone | 30 |
| Magnesium Stearate | 7 |
| Compression weight | 700 mg |

The active ingredient, lactose and pregelatinised starch are blended together and granulated with water. The wet mass is dried and milled. The magnesium stearate and cross-linked polyvinylpyrrolidone are screened through a 250 μm sieve and blended with the granule. The resultant blend is compressed using suitable tablet punches.

EXAMPLE B

Suckable/Chewable Tablets

| | | mg/tablet |
| --- | --- | --- |
| (i) | Active ingredient | 450 |
| | Polyvinylpyrrolidone | 50 |
| | Sweetener/Flavour | qs |
| | Magnesium Stearate | 10 |
| | Mannitol to | 1000 mg |
| | Compression weight | 1000 mg |

The active ingredient, sweetner/flavour and mannitol are blended together and granulated with a solution of polyvinylpyrrolidone. The wet mass is dried, milled and lubricated with magnesium stearate (meshed through a 250 μm sieve). The resultant granule is compressed into tablets using suitable punches.

| | | mg/tablet |
| --- | --- | --- |
| (ii) | Active ingredient | 450 |
| | Hydroxypropyl methylcellulose | 30 |
| | Magnesium Stearate | 10 |
| | Flavour | qs |
| | Xylitol to | 1000 mg |
| | Compression weight | 1000 mg |

The active ingredient, xylitol and flavour are blended together, granulated using a solution of the hydroxypropyl methylcellulose in aqueous ethanol, and dried. The granule is milled, lubricated with magnesium stearate (meshed through a 250 μm sieve) and compressed into tablets using suitable punches.

EXAMPLE C

Capsules

| | | mg/capsule |
| --- | --- | --- |
| (i) | Active ingredient | 450 |
| | Pregelatinised Starch | 70 |
| | Magnesium Stearate | 5 |
| | Fill weight | 525 mg |

The active ingredient and pregelatinised starch are screened through a 500 μm mesh sieve, blended together and lubricated with magnesium stearate (meshed through a 250 μm sieve). The blend is filled into hard gelatin capsules of a suitable size.

| | mg/capsule |
|---|---|
| (ii) Active ingredient | 450 |
| Lactose | 95 |
| Polyvinylpyrrolidone | 25 |
| Cross-linked Polyvinylpyrrolidone | 25 |
| Magnesium Stearate | 5 |
| Fill weight | 600 mg |

The active ingredient and lactose are blended together and wet massed with a solution of polyvinylpyrrolidone. The mass is dried and milled and blended with cross-linked polyvinylpyrrolidone and magnesium stearate (screened through a 250 μm mesh). The resultant blend is filled into hard gelatin capsules of a suitable size.

| Example D Oral Syrup | |
|---|---|
| Active ingredient | 450.0 mg |
| Hydroxypropyl Methylcellulose | 45.0 mg |
| Propyl Hydroxybenzoate | 1.5 mg |
| Butyl Hydroxybenzoate | 0.75 mg |
| Saccharin Sodium | 5.0 mg |
| Sorbitol Solution | 1.0 ml |
| Suitable Buffers | qs |
| Suitable Flavours | qs |
| Purified Water to | 10 ml |

The hydroxpropyl methylcellulose is dispersed in a portion of hot purified water together with the hydroxybenzoates and the solution is allowed to cool to room temperature. The saccharin sodium, flavours and sorbitol solution are added to the bulk solution. The active ingredient is dissolved in a portion of the remaining water and added to the bulk solution. Suitable buffers may be added to control the pH in the region of maxiumum stability. The solution is made up to volume, filtered and filled into suitable containers.

We claim:

1. A salt of a basic histamine $H_2$-receptor antagonist of formula (I)

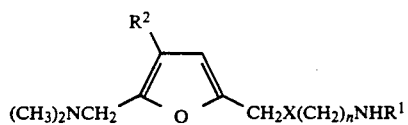

and a complex of bismuth with citric acid or a solvate of such a salt, wherein $R^1$ represents a group of formula

where $R^3$ represents methyl;
$R^2$ represents a methyl group; and
n is 2 and X is sulphur.

2. A pharmaceutical composition which comprises an effective amount of a salt as defined in claim 1 or a solvate thereof together with at least one pharmaceutically acceptable carrier or diluent.

3. A pharmaceutical composition according to claim 2 in a form adapted for oral administration.

4. A method of treating a gastrointestinal disorder which comprises administering to a patient an effective amount to relieve said disorder of a salt as defined in claim 1 or a solvate thereof.

5. A salt of a basic histamine $H_2$-receptor antagonist of formula (I) as defined in claim 1 and a complex of bismuth with citric acid or a solvate of such a salt, said salt having been prepared by reacting said $H_2$-antagonist with a bismuth-citric acid complex.

6. N-[2-[[[5-[(Dimethylamino)methyl]-4-methyl-2-furanyl]methyl]thio]ethyl]-N'-methyl-2-nitro-1,1-ethenediamine-2-hydroxy-1,2,3-propanetricarboxylate bismuth (3+) complex (1:1) (1:1).

* * * * *